United States Patent

Sutter et al.

[11] Patent Number: 4,954,517
[45] Date of Patent: Sep. 4, 1990

[54] MICROEICIDES

[75] Inventors: Marius Sutter, Basel, Switzerland; Bettina Böhlendorf, Braunschweig; Norbert Bedorf, Königslutter; Gerhard Höfle, Braunschweig, all of Fed. Rep. of Germany

[73] Assignees: Gesellschaft für Biotechnologische Forschung mbH, Fed. Rep. of Germany; Ciba-Geigy Corporation, Ardsley, N.Y.

[21] Appl. No.: 405,382

[22] Filed: Sep. 8, 1989

[30] Foreign Application Priority Data

Sep. 9, 1988 [CH] Switzerland ............... 3377/88

[51] Int. Cl.[5] ............... A61K 31/365; C07D 321/00
[52] U.S. Cl. ............... 514/450; 549/214; 549/215; 549/267
[58] Field of Search ............... 549/267, 214, 215; 514/450; 71/88, 77

[56] References Cited

FOREIGN PATENT DOCUMENTS 0282455  9/1988  European Pat. Off. .

Primary Examiner—Glennon H. Hollrah
Assistant Examiner—Amelia A. Owens
Attorney, Agent, or Firm—George R. Dohmann; Edward McC. Roberts

[57] ABSTRACT

A macrocyclic compound of the formula I,

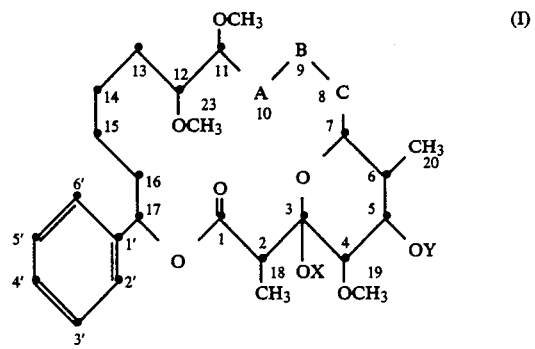

in which the substituents have the following meaning: X is hydrogen or methyl, Y is hydrogen, —CHO, —COCH$_3$, —COCH$_2$OCH$_3$, —COCH$_2$OCH$_3$, —COCH$_2$NH$_2$, benzyl, methyl or a silyl group, and A—B—C is the following C$_3$-chain members:

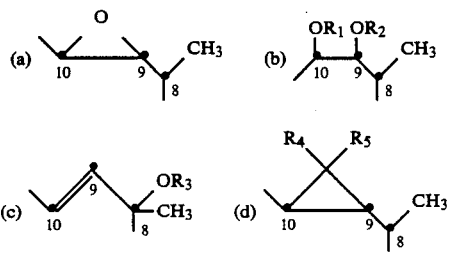

in which R$_1$, R$_2$ and R$_3$, independently of one another, are hydrogen, methyl, —CHO, —COCH$_2$OCH$_3$, —COCH$_2$OCH$_3$, —COCH$_2$NH$_2$ or a silyl group, and R$_4$ and R$_5$ are hydrogen, halogen or —COO(C$_1$—C$_3$) alkyl, is suitable for controlling and preventing plant diseases. A compound of this type can be employed in a customary manner in the form of plant-protecting agents formulated with carrier substances and extenders.

18 Claims, No Drawings

MICROEICIDES

The present invention relates to a macrocyclic compound of the formula I, a process for its preparation, and its use for controlling plant diseases, and plant-microbicidal agents which contain this compound as active compound.

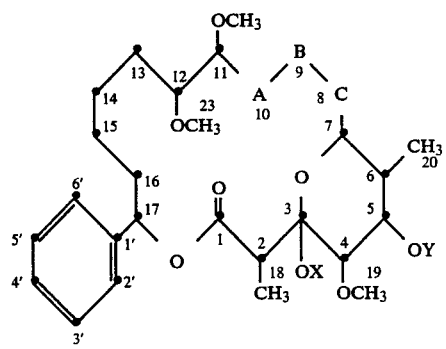

In this formula, X is hydrogen or methyl, Y is hydrogen, —CHO, —COCH$_3$, —COCH$_2$OCH$_3$, —COCH$_2$NH$_2$, benzyl, methyl or a silyl group, and A—B—C is the following C$_3$-chain members:

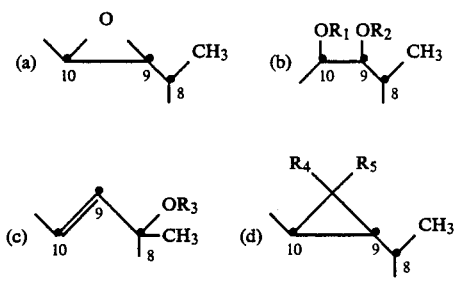

in which R$_1$, R$_2$ and R$_3$, independently of one another, are hydrogen, methyl, —CHO, —COCH$_3$, —COCH$_2$OCH$_3$, —COCH$_2$NH$_2$ or a silyl group, and R$_4$ and R$_5$ are hydrogen, halogen or —COO(C$_1$–C$_3$)alkyl.

Silyl groups are taken to mean radicals which are usually used in natural product syntheses as silyl protecting groups on, for example, hydroxyl groups. Examples which may be mentioned are trimethylsilyl, diphenyl-tert-butylsilyl, bis(isopropyl)methylsilyl, triphenylsilyl, etc. and, in particular, tert-butyldimethylsilyl.

C$_1$–C$_3$alkyl is taken to be methyl, ethyl, propyl or isopropyl.

The compounds of the formula I are derived from the basic structure, known as "soraphen A", of a novel natural macrocyclic compound of the formula

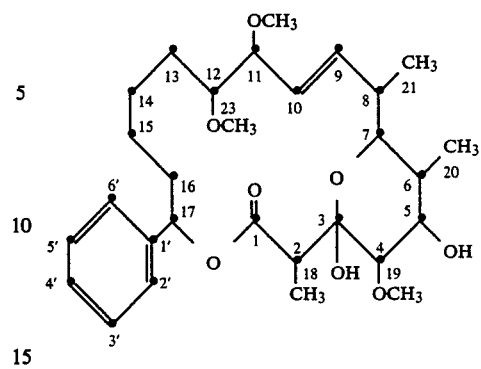

On the basis of its physicochemical data, it is assumed that this specimen has the following configuration:

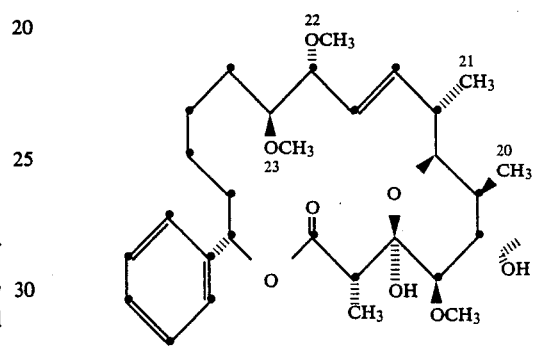

Soraphen A is obtained by microbiological cultivation of a Sorangium (Polyangium) cellulosum strain "So ce 26". This strain has been deposited on Mar. 5, 1987, at "National Collection of Industrial and Marine Bacteria (NCIB)", Torry Research Station, Aberdeen, Great Britain, in compliance with the provisions of the Budapest Convention, deposit No. NCIB 12,411. Sorangium cellulosum belongs to the order of the Myxobaceterales, sub-order Sorangineae, family Polyangiaceae.

"So ce 26" itself, or mutants or recombinants, are the subject-matter of European Patent Application No. EP-A-0,282,455. The strain can be cultured by conventional biological methods, for example in agitated cultures or in fermenters, using nutrient media having a pH of 6–8, at 10–35° C. The procedure is aerobic. The conditions for culturing the microorganism are introduced into the present description as a reference to No. EP-A-0,282,455.

The process according to the invention for the preparation of a compound of the formula I from soraphen A has the following features, optionally and irrespective of the sequence:

(a) carbene adduction, selenium dioxide oxidation, osmium tetroxide oxidation or epoxidation in the 9,10-position, with or without further ring opening of the epoxide formed, and/or, if desired, (b) methylation of the 3-OH group, and/or, if desired, (c) formylation, acetylation, methoxyacetylation, aminoacetylation, methylation, benzylation or silylation of the 5-OH group and/or of the newly formed OH groups in the 8-, 9- or 10-position.

The choice of reaction steps depends on the reaction to be carried out.

If the 9,10-double bond in the formula I is to be converted into a 9,10-epoxide in accordance with definition (a), this can be achieved by oxidation of soraphen A or of a 5-protected (possibly also 3-protected) soraphen A derivative in the temperature range from −30° C. to +100° C., preferably −10° C. to +30° C., and expediently at 0° to 10° C. using $H_2O_2$ or a peracid, such as m-chloroperbenzoic acid or peracetic acid, in inert solvents, such as dichloromethane, toluene, benzene, etc., in the presence or absence of a base, such as $NaHCO_3$, $Na_2HPO_4$ etc. The oxidation can also be carried out using tert-butyl hydroperoxide in the presence of catalysts, such as vanadium(V) complexes, for example starting from vanadyl(IV) acetylacetonate or Mo(VI) complexes, for example starting from molybdenum hexacarbonyl, in inert solvents, such as dry hydrocarbons (for example benzene, toluene or xylene).

If the 9,10-epoxide is to be converted into a 9,10-diol of type (b), the epoxide can be opened using mild Lewis acids, such as $ZnCl_2$, $ZnBr_2$ or $TiCl_4$, in the presence of water.

9,10-Diols can advantageously be obtained from the olefin by reaction with osmium tetroxide at 0° to 100° C., preferably at room temperature. Examples of solvents which can be used are ether, tetrahydrofuran, acetone etc., with or without addition of pyridine.

If compounds of type (c) containing an oxygen function in the 8-position are to be prepared, the 9,10-double bond of "soraphen A" can be oxidized using selenium dioxide in solvents such as acetic acid, acetic anhydride, dioxane or alcohols, with or without addition of water, at 0° to 100° C.

The cyclopropane derivatives mentioned in the definition under (d) can be obtained by reacting appropriate olefins with carbenes. (Houben-Weyl, "Methoden der organischen Chemie" [Methods of Organic Chemistry], Volume 413, p. 98ff].

Carbenes can be prepared in a manner known from the literature, for example starting from diazomethane, which is converted pyrolytically, photolytically or catalytically (for example in the presence of copper, copper(II) sulfate, copper(I) chloride, platinum(IV) chloride or zinc iodide) to $[H_2C]$. Carbenes can also be prepared by the method of Simmon-Smith, in which the methylene diiodide reacts with a zinc/copper pair to form $[H_2C]$.

Halocarbenes ($R_4$ and $R_5$=halogen) can be prepared from appropriately substituted methane derivatives by treatment with bases. Examples of suitable carbene formers are chloroform, bromoform and dichloromethane. Examples of basic components are KOH, alkali metal alcoholates, such as K tert-butylate or alkyllithium, such as n-butyllithium. Halocarbenes can also be prepared from appropriate salts of perhalogenated acetic acids by warming to 50° to 300° C.

Alkoxycarbonylcarbenes ($R_4$ and $R_5$=COOalkyl) can be obtained from appropriate diazoacetic acid esters by catalytic decomposition. Examples of catalysts which can be employed are metallic copper or copper salts, such as $CuSO_4$, or rhodium salts, such as Rh(II) acetate. In all these cases, the solvents used can be the carbene former alone or mixed with inert solvents, such as ethers (diethyl ether, diglyme, dioxane or tetrahydrofuran) or hydrocarbons (for example petroleum ether).

The reaction temperatures for obtaining an using appropriate carbenes are between −50° and +300° C.

Methylation of an already existing hydroxyl group in "soraphen A" can expediently be carried out using methyl iodide in dimethyl sulfoxide at room temperature with addition of a base, such as KOH. Benzylation is advantageously carried out using benzyl bromide.

By customary acylation of an OH group using the appropriate carboxylic acid or using an appropriate acyl halide or acyl anhydride or silylation by reaction of an OH group using the appropriate substituted silane derivative of the formula

which may carry alkyl, phenyl or benzyl on the free bonds, all formyl, acetyl or silyl derivatives as in the definition are obtained, the term acyl halide meaning acyl chloride or acyl bromide and X meaning a silyl leaving group. The silyl leaving groups X include, for example, bromide, chloride and trifluoromethane sulfonate.

O-acylation and O-silylation are carried out in anhydrous media, for example in inert solvents and particularly preferably in aprotic solvents. The reaction advantageously proceeds in the temperature range from 0° C. to 80° C., preferably at 10° C. to 50° C. An organic base is preferably added. Examples which may be mentioned are tertiary amines, such as triethylamine, triethylenediamine, triazole and preferably pyridine, diisopropylamine, 4-dimethylaminopyridine, imidazole, or 1,8-diazocyclo 5.4.0]undec-7-ene (DBU).

Examples of suitable solvents are: ethers and ether-like compounds, such as dialkyl ether (diethyl ether, diisopropyl ether, tert-butyl methyl ether, dimethoxyethane, dioxane, tetrahydrofuran, anisole, etc.); halogenated hydrocarbons, such as chlorobenzene, methylene chloride, ethylene chloride, chloroform, carbon tetrachloride, tetrachloroethylene, etc.; dimethylformamide (=DMF) or sulfoxides, such as dimethyl sulfoxide, it also being possible for aromatic or aliphatic hydrocarbons, such as benzene, toluene, xylenes, petroleum ether, ligroin, cyclohexane, etc., to be present. In some cases, it may be advantageous for the reactions to be carried out under protective gas atmospheres (for example argon, helium, nitrogen, etc.) and/or in absolute solvents.

If acid halides or acid anhydrides are employed for the acylation, the addition of a neutralizing agent has proven advantageous. Tertiary amines, such as trialkylamines, pyridine or pyridine bases, such as 4-dimethylaminopyridine, are expedient reagents.

If interfering functional groups such as OH are in the molecule or in the reactants, they can be masked at the outset, as mentioned above, by acetylation or introduction of other protecting groups, such as, in addition, a silyl group [T. W. Green "Protective Groups in Organic Synthesis", J. Wiley & Sons 1981 (New York)].

If desired, protecting groups such as acyl groups can be removed by mild hydrolysis (generally using, for example, $NH_3$/methanol). Suitable solvents in this substep are, in particular, aprotic representatives, such as dichloromethane, acetonitrile, benzene, toluene, nitromethane, dioxane, THF and ethylene glycol dimethyl ether; diethyl ether is particularly suitable.

Silyl groups can be removed by treatment with acid or fluoride ions, preferably hydrofluoric acid in acetonitrile or tetrabutylammonium fluoride in tetrahydrofuran (=THF).

The list of all the abovementioned methods is not a limiting one. If desired, end products can be purified in a customary manner, for example by washing, digestion, extraction, recrystallization, chromatography, etc.

The preparation processes described, including all sub-steps, for obtaining compounds of the formula I in all possible stereoisomeric forms are part of the present invention.

The invention relates, in particular, to a compound of the formula I in which Y is hydrogen, —CHO, —COCH$_2$, benzyl, methyl or a silyl protecting group, and R$_1$, R$_2$ and R$_3$ independently of one another, are hydrogen, methyl, —CHO, —COCH$_2$ or a silyl protecting group, while X, R$_4$ and R$_5$ are as defined above (sub-group Ia).

A further important group of compounds within the context of the formula I is that in which A—B—C is either

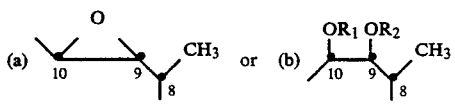

where R$_1$ and R$_2$, independently of one another, are hydrogen, methyl, —CHO, —COCH$_3$, —COCH$_2$OCH$_3$, —COCH$_2$NH$_2$, while X and Y are as defined above (sub-group Ib). In this group, those are preferred in which X is hydrogen (sub-group Ibb).

In addition, compounds of the formula I are important in which A—B—C is either

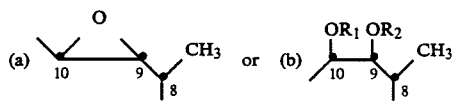

X is hydrogen and Y, R$_1$ and R$_2$, independently of one another, are hydrogen, methyl, —CHO, —COCH$_3$ or a silyl protecting group (subgroup Ic).

Within sub-group Ic, those are preferred in which Y is hydrogen, methyl, —CHO, —COCH$_3$ or a silyl protecting group, and R$_1$ and R$_2$ are identical and are hydrogen, methyl or formyl (sub-group Icc).

Of the preferred individual compounds, the following should be mentioned:
9,10-epoxy-soraphen A,
9,10-dihydroxy-soraphen A,
5,9,10-triformyl-soraphen A,
5,9,10-triacetyl-soraphen A,
9,10-epoxy-soraphen A 5-acetate,
9,10-epoxy-soraphen A 5-formate,
9,10-bis(methoxyacetoxy)-soraphen A 5-methoxyacetate, and
9,10-bis(aminoacetoxy)-soraphen A 5-aminoacetate.

It should be noted that the macrocyclic soraphens of the formula I are normally in the hemiacetal form indicated, but this form can undergo a reversible ring opening in accordance with the equation

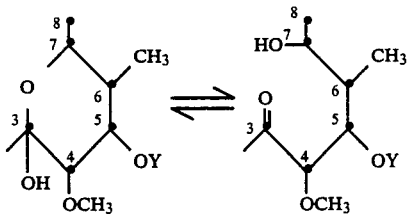

Depending on the preparation method or work-up method, and the pH and on the solvent, the soraphens are produced in one or other form or as a mixture of the two forms. The shift of the $^{13}$C NMR signal in the 3-position and of the $^1$H NMR signals in certain other positions is characteristic of ring opening. In soraphen A, for example, the following changes are observed: $^{13}$C NMR(CDCl$_3$, δ in ppm) 99.5→203.1(3-C).$^1$H NMR(CDCl$_3$, δ in ppm): 3,14→3,72(2-H); 3.18→4.5(4-H); 3.83→3.16 (7-H); 5.86→5.7 (17-H). Similar shifts are also observed in the soraphen derivatives of the formula I described herein. The formula I of the present invention always covers both the 3-hemiacetal form which is preferred at low pH values and also the opened 3-keto-7-hydroxyl form.

It has been found that compounds of the formula I have a biocidal spectrum against phytopathogenic microorganisms, in particular against fungi, which is highly favourable for practical requirements. They have highly advantageous curative, systemic and in particular preventive properties and are employed for the protection of numerous crop plants. Using the active substances of the formula I, pests which occur on plants or parts of plants (fruits, flowers, foliage, stalks, tubers, roots) of various crops can be brought under control or destroyed, additional growth of parts of plants which occurs later also being kept free from phytopathogenic microorganisms.

As microbicides, the active substances of the formula I are active, for example, against the phytopathogenic fungi belonging to the following classes: Fungi imperfecti (for example in particular Botyritis, furthermore Pyricularia, Helminthosporium, Fusarium, Septoria, Cercospora and Alternaria); Basidiomycetes (for example Rhizoctonia, Hemileia, Puccinia). Moreover, they are active against the class of the Ascomycetes (for example in particular Venturia and Erysiphe, furthermore Podosphaera, Monilinia, Uncinula) and of the Oomycetes (for example Phytophthora, Plasmopara). The compounds of the formula I can furthermore be employed as seed-dressing agents for treating of seeds (fruits, tubers, grains) and of cuttings in order to protect them from fungal infections, as well as soil-borne phytopathogenic fungi.

The invention also relates to the agents which contain compounds of the formula I in one of the possible stereoisomeric forms as the active ingredient, in particular plant-protecting agents, as well as the use thereof in the agricultural sector or in related fields.

This also applies to a process for the treatment of plants which is distinguished by the application of the novel compounds of the formula I or of the corresponding novel agents.

Examples of target crops for the plant protection use disclosed in this publication, within the scope of this invention, are the following plant species: cereals (wheat, barley, rye, oats, rice, maize, sorghum and related species); beet (sugar-beet and fodder beet); pomaceous fruit, stone fruit and soft fruit (apples, pears, plums, peaches, almonds, cherries, strawberries, raspberries and blackberries); pulses (beans, lentils, peas, soya beans); oil crops (oil seed rape, mustard, poppy, olives, sunflowers, coconuts, castor, cocoa, peanuts); the gourd family (pumpkin, cucumbers, melons); fibre plants (cotton, flax, hemp, jute); citrus fruit (oranges, lemons, grapefruit, tangerines); various vegetables (spinach, lettuce, asparagus, cabbage species, carrots, onions, tomatoes, potatoes, paprika); the Lauraceae (avocado, Cinnamonium, camphor) or plants such as tobacco, nuts, coffee, pineapple, sugar cane, tea, pepper, vines, hops, the banana family and plants which yield natural rubber, as well as ornamental plants (Compositae). This enumeration does not represent any limitation.

Active substances of the formula I are customarily used in the form of compositions and can be applied to the area or plant to be treated either simultaneously or in succession with other active substances. These other active substances can be fertilizers, suppliers of trace elements or other preparations which influence plant growth. In this context, it is also possible to use selective herbicides as well as insecticides, fungicides, bactericides, nematicides, molluscicides or mixtures of a plurality of these preparations, if desired together with further carriers conventionally used in the art of formulation, surfactants or other additives which assist application.

Suitable carriers and additives can be solid or liquid and correspond to the substances advantageously used in the art of formulation, for example natural or regenerated mineral substances, solvents, dispersants, wetting agents, tackifiers, thickeners, binders or fertilizers.

A preferred method of applying an active substance of the formula I or an agrochemical agent which contains at least one of these active substances, is application onto the foliage (leaf application). In this context, the frequency of application and the dosage rate depend on the infection pressure of the specific pathogen. However, the active substances of the formula I can also enter the plant via the soil and the root system (systemic action), by drenching the site where the plant grows with a liquid preparation, or by incorporating the substances in solid form into the soil, for example in the form of granules (soil application). Compounds of the formula I can also be applied to seeds (coating), either by immersing the grains in a liquid preparation of the active substance or by coating them with a solid preparation.

In this context, the compounds of the formula I are employed in unaltered form or, preferably, together with the adjuvants conventionally used in the art of formulation. For this purpose, they are expediently processed in a known manner, for example to give emulsion concentrates, spreadable pastes, directly sprayable or dilutable solutions, dilute emulsions, wettable powders, soluble powders, dusts, granules or encapsulations, for example in polymeric substances. The application methods, such as spraying, misting, dusting, scattering, brushing or watering, as well as the type of the agents, are chosen to suit the intended use and the circumstances which prevail. Advantageous application rates are generally at around 10 g to 500 g of active substance (a.s.) per hectare, preferably at around 50 g to 200 g of a.s./ha.

The preparations, i.e. the agents containing the active substance of the formula I and a solid or liquid additive, are prepared in a known manner.

Possible solvents are: aromatic and aliphatic hydrocarbons, for example xylene mixtures, cyclohexane or paraffins; also alcohols and glycols as well as their ethers and esters, such as ethanol, ethylene glycol, ethylene glycol monomethyl ether or ethylene glycol monoethyl ether, or acetic esters; ketones, such as cyclohexanone, strongly polar solvents, such as N-methyl-2-pyrrolidone, dimethyl sulfoxide or dimethylformamide, as well as epoxidized and unepoxidized vegetable oils, such as epoxidized coconut oil or soya oil; or water.

Solid carriers which are generally used, for example for dusting agents and dispersible powders, are ground natural minerals, such as calcite, talc, kaolin, montmorilonite or attapulgite. To improve the physical properties, it is also possible to add highly-disperse silicic acid or highly-disperse absorptive polymers. Possible adsorptive, granulated granule carriers are porous types, for example pumice, ground brick, sepiolite or bentonite, possible non-sorptive carriers are, for example, calcite or sand. In addition, a large range of pre-granulated materials of inorganic nature, such as, in particular, dolomite, or comminuted plant residues, can be used.

Suitable surface-active compounds are non-ionogenic or cation-active and/or anion-active surfactants having good emulsifying, dispersing and wetting properties, depending on the type of the active substance of the formula I to be formulated. Surfactants are also understood as meaning mixtures of surfactants.

Suitable anionic surfactants can be either so-called water-soluble soaps or water-soluble synthetic surface-active compounds.

More frequently, however, so-called synthetic surfactants are used, in particular alkane sulfonates, fatty alcohol sulfates, sulfonated benzimidazole derivatives or alkyl sulfonates.

Possible non-ionic surfactants are polyglycol ether derivatives of aliphatic or cycloaliphatic alcohols, of saturated or unsaturated fatty acids and of alkylphenols, which can contain 3 to 30 glycol ether groups and 8 to 20 carbon atoms in the (aliphatic) hydrocarbon moiety and 6 to 18 carbon atoms in the alkyl moiety of the alkylphenols.

Further examples of non-ionic surfactants which may be mentioned are nonylphenol polyethoxyethanols, castor oil polyglycol ethers, polypropylene/polyethylene oxide adducts, tributylphenoxypolyethyleneethanol, polyethylene glycol and octylphenoxypolyethoxyethanol.

Further suitable substances are also fatty acid esters of polyoxyethylene sorbitan, such as polyoxyethylene sorbitan trioleate.

Further surfactants which are used in the art of formulation are known to those skilled in the art or can be found in the specialized literature.

As a rule, the agrochemical preparations contain 0.1 to 95% of active substance of the formula I, 99.9 to 5% of a solid or liquid additive and 0 to 25% of a surfactant.

While fairly concentrated agents are preferred as a commercial good, the end consumer, as a rule, uses dilute agents.

The agents can also contain further additives, such as stabilizers, defoamers, viscosity regulators, binders, tackifiers as well as fertilizers or other active substances, for obtaining specific effects.

The examples which follow are intended to illustrate the invention in greater detail without imposing any limitation.

1. Preparation Examples

H-1. Preparation of 9,10-dihydroxy-soraphen A (Comp. 1)

100 mg of osmium tetroxide and 2 ml of pyridine are added with gentle stirring to 21 mg of soraphen A in 10 ml of diethyl ether, and the mixture is left to stand at room temperature for 8 days. The supernatant solution is removed by pipette, and the precipitate formed is dissolved in 3 ml of dichloromethane and reprecipitated by carefully adding hexane dropwise. After the solvent has been removed, the precipitate is dried.

A solution of 1.8 g of NaHSO$_3$ in 30 ml of water and 20 ml of pyridine is added to the precipitate, and the mixture is stirred at room temperature for 25 minutes. The solution is then extracted three times with 50 ml of dichloromethane in each case. The combined organic phases are washed once with 30 ml of saturated NaCl solution, dried over Na$_2$SO$_4$ and evaporated. The oil which remains is purified on silica gel using ethyl acetate/hexane (3:1) as eluant: 5.1 mg of end product.

R$_f$(hexane/ethyl acetate=1:2):0.12
MS:M$^+$=554

| $^1$H NMR (Deuteroacetone): | 5.85 ppm t, J = 7 Hz, H—C$^{17}$) |
| --- | --- |
| 250 MHz | 3.46 ppm ⎫<br>3.41 ppm ⎬ (3s)(3-OCH$_3$)<br>3.39 ppm ⎭ |

$^{13}$C NMR (Deuteroacetone): 69.2; 70.3; 73.9; 74.7; 75.2; 77.1; 81.7; 84.1(8d); 101.1(s).

H-2. Preparation of 5-tert-butyldimethylsilyl-9,10-epoxy-soraphen A (Comp. 26)

1.1 g of imidazole and 1.6 g of tert-butyldimethylsilyl chloride are added to 1.0 g of soraphen A in 5 ml of DMF at room temperature. The mixture is stirred for 3 days and then poured on to diethyl ether, washed with 1N hydrochloric acid, then with saturated sodium hydrogen carbonate solution and saturated sodium chloride solution, dried over sodium sulfate and filtered, and the solvent is removed. Chromatography gives 0.84 g of 5-tert-butyldimethylsilyl-soraphen A.

0.51 g of this compound is dissolved in 5 ml of methylene chloride, and 0.82 g of m-chloroperbenzoic acid is added. When the reaction is complete, the mixture is diluted with ethyl acetate, washed with saturated sodium hydrogen carbonate solution and dried over sodium sulfate, and the solvent is removed. Chromatography gives 0.34 g of product.

H-3. Preparation of 9,10-epoxy-soraphen A (Comp. 7)

1 ml of 1N tetrabutylammonium fluoride solution in THF is added to 10 mg of compound No. 26, and the mixture is stirred at room temperature for 20 minutes. The mixture is taken up on ethyl acetate, washed with saturated sodium chloride solution, dried over sodium sulfate and evaporated. Chromatography gives 2.7 mg of 9,10-epoxy-soraphen A.

H-4. Preparation of 5-tert-butyldimethylsilyl-9,10-dihydroxy-soraphen A (Comp. No. 35)

1.11 g of compound No. 26 are dissolved in 2 ml of benzene, and 3.8 g of zinc bromide are added. The suspension is stirred overnight at room temperature, filtered and evaporated. Chromatography gives 0.34 g of compound No. 35, from which 9,10-dihydroxy-soraphen A, which is epimeric to compound 1 and in which the two OH groups are on the same side of the molecular plane, is obtained by desilylation using fluoride.

TABLE 1

| Comp. No. | R$_f$(solv.) | MS(FD) | $^1$H NMR (Deuteroacetone) |
| --- | --- | --- | --- |
| 1 | 0.27 (2) | | 5.85(H-17) 5.60(OH) 5.06(OH) 4.24 |
| 7 | 0.32 (1) | 537(M$^+$ + H) | 6.02(H-17) 5.76(OH) 5.36(OH) 4.36(H-5) 4.08(H-7) |
| 9 | 0.66 (1) | 579(M$^+$ + H) | 5.88(H-17) 5.11(OH) 4.21(H-7) |
| 17 | 0.30 (2) | | 5.83(H-17) 5.17(OH) 4.80 4.72 |
| 26 | 0.27 (3) | 651(M$^+$ + H) | 6.02(h-17) 5.55(OH) 4.45(H-5) 4.08(H-7) |
| 27 | 0.38 (2) | 551(M$^+$ + H) | 6.03(H-17) 5.10(OH) 3.90(H-7) |
| 28 | 0.45 (2) | 668(M$^+$)* | 5.86(H-17) 5.34(OH) 4.34 4.18 |
| 31 | 0,51 (1) | 720(M$^+$)* | 6.10(H-17) 5.40(HO) 5.22(3 OH) 4.48(H-7) 4.32(H-5) |
| 35 | 0.40 (1) | 668(M1$^+$)* | 6.10(H-17) 5.50(OH) 4.74(H-7) 4.42(H-5) 4.12 |

(1) ethyl acetate/hexane 1:1
(2) ethyl acetate/hexane 3:1
(3) diethyl ether/hexane 1:1
*CI The soraphen A derivatives mentioned in the Table below can be obtained in this manner or by one of the methods indicated above.

TABLE 2

| No. | X | Y | ABC |
| --- | --- | --- | --- |
| 1 | H | H | OH OH CH$_3$ |
| 2 | H | CHO | OCHO OCHO CH$_3$ |
| 3 | H | COCH$_3$ | OC(O)CH$_3$ OC(O)CH$_3$ CH$_3$ |

TABLE 2-continued

| No. | X | Y | ABC |
|---|---|---|---|
| 4 | CH₃ | CH₃ | OCH₃, OCH₃, CH₃ substituents on chain |
| 5 | H | Si(CH₃)₃ | OSi(CH₃)₃, OSi(CH₃)₃, CH₃ substituents on chain |
| 6 | H | Si—⊢ (trisubstituted Si) | OSi(CH₃)₃, OSi(CH₃)₃, CH₃ substituents on chain |
| 7 | H | H | epoxide O, CH₃ substituent on chain |
| 8 | CH₃ | CH₃ | epoxide O, CH₃ substituent on chain |
| 9 | H | COCH₃ | epoxide O, CH₃ substituent on chain |
| 10 | H | COCH₃ | OC(O)CH₃, OH, CH₃ substituents on chain |
| 11 | H | COCH₃ | OH, OC(O)CH₃, CH₃ substituents on chain |
| 12 | H | COCH₃ | OC(O)CH₃, OSi(CH₃)₃, CH₃ substituents on chain |
| 13 | H | H | OH, CH₃ on chain with double bond |
| 14 | H | H | OCHO, CH₃ on chain with double bond |
| 15 | CH₃ | CH₃ | OH, CH₃ on chain with double bond |
| 16 | H | COCH₃ | OSi(CH₃)₂(tert. butyl), CH₃ on chain with double bond |
| 17 | H | O benzyl | OH, OH, CH₃ substituents on chain |
| 18 | H | H | OH, O benzyl, CH₃ substituents on chain |
| 19 | H | H | O benzyl, OH, CH₃ substituents on chain |
| 20 | H | H | Cl, Cl (cyclopropane), CH₃ substituent |

TABLE 2-continued
| No. | X | Y | ABC |
|---|---|---|---|
| 21 | H | H |  |
| 22 | H | COCH₃ | 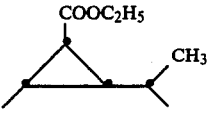 |
| 23 | H | H | 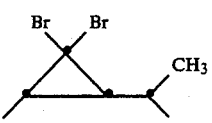 |
| 24 | H | H | 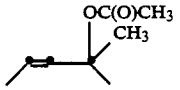 |
| 25 | H | H | 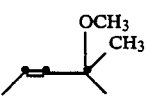 |
| 26 | H |  | 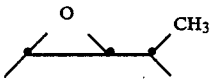 |
| 27 | H | CH₃ | 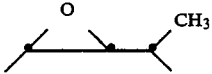 |
| 28 | H |  | 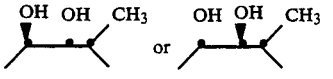 |
| 29 | H | CH₃ | 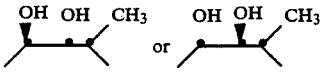 |
| 30 | H |  | 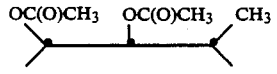 |
| 31 | H |  | 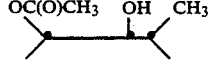 |
| 32 | H |  | 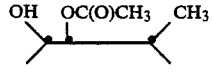 |
| 33 | H |  | 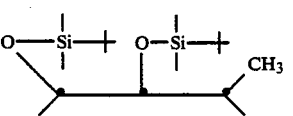 |
| 34 | H |  | 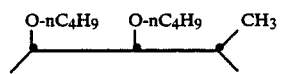 |

TABLE 2-continued

| No. | X | Y | ABC |
|---|---|---|---|
| 35 | H | Si—⊢ | OH OH CH₃ / or / OH OH CH₃ |
| 36 | H | CH₃ | OCH₃ OCH₃ CH₃ |
| 37 | H | —CO—CH₂—OCH₃ | OC(O)CH₂OCH₃  OC(O)CH₂OCH₃  CH₃ |
| 38 | H | —CO—CH₂—NH₂ | OC(O)CH₂NH₂  OC(O)CH₂NH₂  CH₃ |
| 39 | H | —CHO | O  CH₃ |
| 40 | H | —CO—CH₂—OCH₃ | O  CH₃ |
| 41 | H | —CO—CH₂—NH₂ | O  CH₃ |

Si—⊢ = tert-butyl-dimethylsilyl

2. Formulation examples of the active substance of the formula I (%=percent by weight) ["Active substance" in the following denotes an active substance from the previous Table 2]

| 2.1 Emulsion concentrates | (a) | (b) | (c) |
|---|---|---|---|
| Active substance | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from such concentrates by dilution with water.

| 2.2 Solutions | (a) | (b) | (c) | (d) |
|---|---|---|---|---|
| Active substance | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Mineral oil (boiling range 160–190° C.) | — | — | 94% | — |

(MW = molecular weight)

The solutions are suitable for application in the form of microdroplets.

| 2.3 Granules | (a) | (b) |
|---|---|---|
| Active substance | 5% | 10% |
| Kaolin | 94% | — |
| Highly-disperse silicic acid | 1% | — |
| Attapulgite | — | 90% |

The active substance is dissolved in methylane chloride, the solution is sprayed onto the carrier, and the solvent is then evaporated in vacuo.

| 2.4 Dusts | (a) | (b) |
|---|---|---|
| Active substance | 2% | 5% |
| Highly-disperse silicic acid | 1% | 5% |
| Talc | 97% | — |
| Kaolin | — | 90% |

Intimate mixing of the carrier substances with the active substance gives ready-to-use dusts. With the further addition of the three carrier substances, these dusts can be ground to give dusts ready for application containing 0.001% of active substance.

| 2.5 Wettable powders | (a) | (b) | (c) |
|---|---|---|---|
| Active substance | 25% | 50% | 75% |
| Na ligninsulfonate | 5% | 5% | —% |
| Na laurylsulfate | 3% | — | 5% |
| Na Diisobutylnaphthalenesulfonate | — | 6% | 10% |
| Octylphenol polyethylene glycol ether (7–8 mol of ethylene oxide) | — | 2% | —% |
| Highly-disperse silicic acid | 5% | 10% | 10% |
| Kaolin | 62% | 27% | — |

The active substance is thoroughly mixed with the additives, and the mixture is thoroughly ground in a suitable mill. This gives wettable powders which can be diluted with water to give suspensions of any desired concentration.

| 2.6 Coated granules | |
|---|---|
| Active substance | 3% |
| Polyethylene glycol (MW 200) | 3% |
| Kaolin | 94% |

(MW = molecular weight)

In a mixer, the kaolin moistened with polyethylene glycol is evenly coated with the finely-ground active substance. In this manner, dust-free coated granules are obtained.

| 2.7 Suspension concentrate | |
|---|---|
| Active substance | 40% |
| Ethylene glycol | 10% |
| Nonylphenol polyethylene glycol ether (15 moles of ethylene oxide) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is intimately mixed with the additives. This gives a suspension concentrate, from which suspensions of any desired concentration can be prepared by dilution with water.

3. Biological examples on plants (In the following "active substance" denotes a preparation from Table 2, unless stated otherwise).

Example 3.1: Action against *Puccinia graminis* on wheat
(a) Residual-protective action
6 days after sowing, wheat plants are sprayed with a spray liquor (0.02% of active ingredient) prepared from a wettable powder of the active substance. After 24 hours, the treated plants are infected with a uredospore suspension of the fungus. After incubation for 48 hours at 95-100% relative atmospheric humidity and about 20° C., the infected plants are placed in a greenhouse at about 22° C. The development of rust pustules is assessed 12 days after infection.

(b) Systemic action
5 days after sowing, a spray liquor (0.006% active ingredient relative to the soil volume) which is prepared from a wettable powder of the active substance, is poured on to wheat plants. After 48 hours, the treated plants are infected with a uredospore suspension of the fungus. After incubation for 48 hours at 95-100% relative atmospheric humidity and about 20° C., the infected plants are placed in a greenhouse at about 22° C. The development of rust pustules is assessed 12 days after the infection.

In both experiments, fungal infestation was inhibited completely by active substance of the formula I. In experiment (a), compounds nos. 1, 2, 7, 36 and 37 showed complete inhibition (0-5%), even at a concentration of 0.006%.

In contrast, untreated, infected control plants showed 100% infestation with Puccinia Example 3.2: Action against Phytophthora on tomato plants
(a) Residual-protective action
After 3 weeks' growing period, tomato plants were sprayed with a spray liquor (0.02% of active ingredient) which had been prepared from a wettable powder of the active substance. After 24 hours, the treated plants were infected with a Sporangia suspension of the fungus. Fungal infestation was assessed after the infected plants had been incubated for 5 days at 90-100% relative atmospheric humidity and 20° C.

(b) Systemic action
After 3 weeks' growing period, a spray liquor (0.006% of active ingredient relative to the soil volume) which had been prepared from a wettable powder of the active substance, was poured onto tomato plants. Care was taken that the spray liquor did not come into contact with the above-ground parts of the plants. After 48 hours, the treated plants were infected with a Sporangia suspension of the fungus. Fungal infestation was assessed after the infected plants had been incubated for 5 days at 90-100% relative atmospheric humidity and 20° C.

In both experiments, no fungal infestation was observed during the evaluation.

Example 3.3: Action against Plasmopara viticola on vines
Residual-protective action
Vine seedlings in the 4-5 leaf stage were sprayed with a spray liquor (0.006% of active ingredient) which had been prepared from a wettable powder of the active substance. After 24 hours, the treated plants are infected with a Sporangia suspension of the fungus. After the plants have been incubated for 6 days at 95-100% relative atmospheric humidity and 20° C., the fungal infestation is assessed.

In contrast to the untreated, infected control plants where fungal infestation was 100%, the plants which had been treated with active substance I were free from infestation.

Example 3.4: Action against *Cercospora arachidicola* on peanut plants
Residual-protective action
Peanut plants 10-15 cm in height are sprayed with a spray liquor (0.006% of active ingredient) which has been prepared from a wettable powder of the active substance, and, 48 hours later, infected with a Conidia suspension of the fungus. The infected plants are incubated for 72 hours at about 21° C. and a high atmospheric humidity and then placed in a greenhouse until the typical leaf spots occur. The fungicidal action is assessed 12 days after the infection with regard to number and size of the spots which occur.

The plants which had been treated with the active substance I were free from infestation. With compound nos. 1, 2, 7, 27, 29 and 36 to 41, fungal infestation was completely inhibited, even at a concentration of 0.002% of active substance (0-5% infestation). In contrast, untreated, infected control plants showed infestation with Cercospora of 100%.

Example 3.5: Action against *Venturia inaequalis* on apple shoots
Residual-protective action
Apple seedlings having fresh shoots of 10-20 cm in length are sprayed with a spray liquor (0.02% of active ingredient) which has been prepared from a wettable powder of the active substance. After 24 hours, the treated plants are infected with Conidia suspension of the fungus. The plants are then incubated for 5 days at 90-100% relative atmospheric humidity and placed for 10 more days in a greenhouse at 20-24° C. Scab infestation is assessed 15 days after the infection.

The cuttings treated with the active substance I were free from infestation.

Example 3.6: Action against *Botrytis cinerea* on apple fruits

Residual-protective action

Artificially damaged apples are treated by applying dropwise a spray liquor (0.006% of active ingredient) which has been prepared from a wettable powder of the active substance, to the damaged points. The treated fruits are then inoculated with a spore suspension of the fungus and incubated for one week at high atmospheric humidity and about 20° C. In the evaluation, the damaged points which show signs of rot are counted, and the fungicidal action of the test substance is calculated therefrom.

Active substance I completely inhibited the growth of the fungi. With active substance nos. 1, 2, 3, 4, 6, 7, 8, 9, 17, 26, 27, 28, 29, 30 and 34–41, fungal infestation was inhibited completely (0–5% infestation) even at a concentration of 0.002%.

Example 3.7: Action against *Erysiphae graminis* on barley (a) Residual-protective action Barley plants approximately 8 cm in height are sprayed with a spray liquor (0.006% of active ingredient) which has been prepared from a wettable powder of the active substance. After 3–4 hours, the treated plants are dusted with Conidia of the fungus. The infected barley plants are placed in a greenhouse at about 22° C., and fungal infestation is assessed after 10 days.

(b) Systemic action

A spray liquor (0.002% of active ingredient relative to the soil volume) which has been prepared from a wettable powder of the active substance, is poured onto barley plants approximately 8 cm in height. Care was taken that the spray liquor did not come into contact with the above-ground parts of the plants. After 48 hours, the treated plants are dusted with Conidia of the fungus. The infected barley plants are placed in a greenhouse at about 22° C., and fungal infestation is assessed after 10 days.

In both experiments, the plants were free from infestation, and the control plants were completely infected. In Experiment (a), active substances nos. 1, 2, 3, 4, 7, 8, 9, 17, 26, 27, 29, 30 and 34–41, caused complete inhibition of fungal infestation (0–5% infestation), even at a concentration of 0.002%.

Example 3.8: Action against *Rhizoctonia solani* (soil-borne fungus on rice plants)

Protective-local soil application

A spray liquor (0.002% of active ingredient) which has been prepared from a preparation of the active substance, is poured onto 12-day old rice plants without contaminating the above-ground parts of the plants. To infect the treated plants, a suspension of mycelium and sclerotia of R. solani is placed on the soil surface. After incubation for 6 days at 27° C. (day) and 23° C. (night) and 100% relative atmospheric humidity (humid chamber) in a growth cabinet, the fungal infestation on leaf sheath, leaves and stem is assessed.

Almost no infestation occurred after treatment with active substance I Compound no. 7 completely inhibited infestation.

We claim:

1. A macrocyclic compound of the formula I

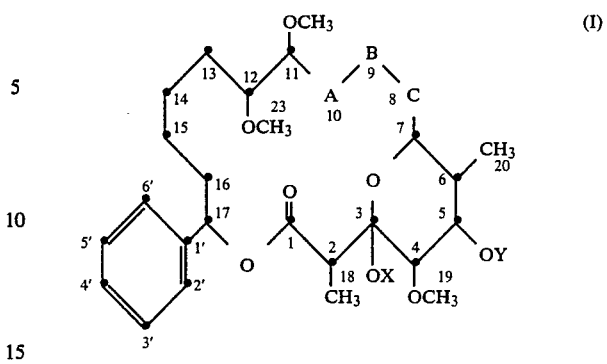

wherein said macrocyclic compound is in the 3-hemiacetal form of formula I or the opened 3-keto-7-hydroxyl form or a mixture of both forms and in which the substituents have the following meanings: X is hydrogen or methyl, Y is hydrogen, —CHO, —COCH$_3$, —COCH$_2$OCH$_3$, —COCH$_2$NH$_2$, benzyl, methyl or a silyl protecting group, and A—B—C is the following C$_3$-chain members:

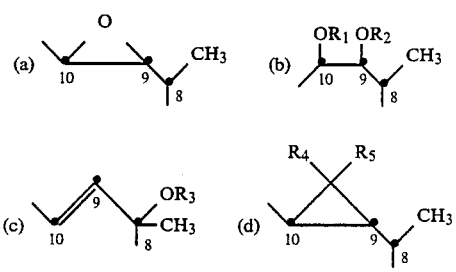

in which R$_1$, R$_2$ and R$_3$, independently of one another, are hydrogen, methyl —CHO, —COCH$_3$, —COCH$_2$OCH$_3$, —COCH$_2$NH$_2$ or a silyl protecting group, and R$_4$ and R$_5$ are hydrogen, halogen or -COO(C$_1$—C$_3$)alkyl.

2. A compound of the formula I according to claim 1, in which Y is hydrogen, —CHO, —COCH$_3$, benzyl, methyl or a silyl protecting group, and R$_1$, R$_2$ and R$_3$, independently of one another, are hydrogen, methyl, —CHO, —COCH$_3$ or a silyl protecting group, while X, R$_4$ and R$_5$ are as defined above.

3. A compound of the formula I according to claim 1, in which A—B—C is either

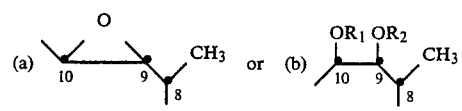

where R$_1$ and R$_2$, independently of one another, are hydrogen, methyl, —CHO, —COCH$_3$, —COCH$_2$OCH$_3$, or —COCH$_2$NH$_2$, while X and Y are as defined above.

4. A compound according to claim 3, in which X is hydrogen.

5. A compound according to claim 1, in which A—B—C is either

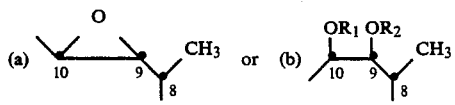

X is hydrogen, and Y, $R_1$ and $R_2$, independently of one another, are hydrogen, methyl, —CHO, —COCH$_3$ or a silyl protecting group.

6. A compound according to claim 5, in which Y is hydrogen, methyl, —CHO, —COCH$_3$ or a silyl protecting group, and $R_1$ and $R_2$ are identical and are hydrogen, methyl or formyl.

7. A compound selected from
9,10-epoxy-soraphen A,
9,10-dihydroxy-soraphen A,
5,9,10-triformyl-soraphen A,
5,9,10-triacetyl-soraphen A,
9,10-epoxy-soraphen A 5-acetate, according to claim 2.

8. A compound selected from
5-methoxy-9,10-epoxy-soraphen A,
5-methoxy-9,10-dihydroxy-soraphen A,
5,9,10-trimethoxy-soraphen A,
9,10-epoxy-soraphen A 5-formate,
9,10-bis(methoxyacetoxy)-soraphen A 5-methoxyacetate, and
9,10-bis(aminoacetoxy)-soraphen A 5-aminoacetate. according to claim 1.

9. A compound of claim 1 which is in the opened 3-keto-7-hydroxyl form.

10. A compound of claim 1 which is in the hemiacetal form of formula I.

11. A compound of claim 1 which is a mixture of the hemiacetal and 3-keto-7-hydroxyl forms of the compound.

12. A process for controlling or preventing plant diseases wherein a compound of the formula I according to claim 1 is applied to the plant, to parts of the plant or to their location.

13. A process according to claim 12, wherein a compound according to claim 2 is applied.

14. A composition for controlling and preventing plant diseases caused by phytopathogenic microorganisms which comprises an effective amount of a compound of claim 1, together with a suitable carrier.

15. A composition for controlling and preventing plant diseases caused by phytopathogenic microorganisms which comprises an effective amount of a compound of claim 2, together with a suitable carrier.

16. A composition for controlling and preventing plant diseases caused by phytopathogenic microorganisms which comprises an effective amount of a compound of claim 7, together with a suitable carrier.

17. A composition for controlling and preventing plant diseases caused by phytopathogenic microorganisms which comprises an effective amount of a compound of claim 3, together with a suitable carrier.

18. A composition for controlling and preventing plant diseases caused by phytopathogenic microorganisms which comprises an effective amount of a compound of claim 8, together with a suitable carrier.

* * * * *